(12) United States Patent
Clendennen et al.

(10) Patent No.: US 7,667,067 B1
(45) Date of Patent: Feb. 23, 2010

(54) COSMETIC EMULSIFIERS

(75) Inventors: Stephanie Kay Clendennen, Kingsport, TN (US); Neil Warren Boaz, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 12/393,631

(22) Filed: Feb. 26, 2009

(51) Int. Cl.
 *C07C 229/00* (2006.01)
 *A61K 6/00* (2006.01)
 *A01N 25/00* (2006.01)
(52) U.S. Cl. .................. 560/155; 424/401; 514/785
(58) Field of Classification Search ............. 560/155; 424/401; 514/785
See application file for complete search history.

(56) References Cited

U.S. PATENT DOCUMENTS 4,564,477 A * 1/1986 Takigawa et al. ............ 554/35

FOREIGN PATENT DOCUMENTS

| EP | 1 249 488 | 10/2002 |
| EP | 1 892 236 | 2/2008 |
| JP | 5132865 | 5/1993 |
| JP | 2002 114647 | 4/2002 |

OTHER PUBLICATIONS

Jandke, Joachim and Spiteller, Gerhard; Liebigs Annalen der Chemie; 1988; 11; pp. 1057-60.

* cited by examiner

*Primary Examiner*—Jafar Parsa
(74) *Attorney, Agent, or Firm*—Brett L Nelson; Bernard J. Graves, Jr.

(57) ABSTRACT

A composition, process of preparation, and utility of salts of fatty acid esters of amino-alcohols such as dimethylaminoethanol (DMAE) as emulsifiers useful for formulating with lipids and waxes is described. DMAE fatty acid esters were prepared enzymatically in the absence of added solvent, and then salified directly with carboxylic acids to form the salts. The compounds were used to make stable emulsions with a variety of cosmetically acceptable lipids.

17 Claims, No Drawings

COSMETIC EMULSIFIERS

FIELD OF THE INVENTION

The present invention relates to fatty acid ester salts of amino-alcohols, preparation thereof, and the use thereof as emulsifiers useful for formulating with lipids and waxes.

BACKGROUND

Within the field of cosmetic formulations, there is an increasing need for preparation of ingredients that avoid or at least reduce organic solvent and toxic reagent use, employ reagents that are themselves biocompatible and that optimally use starting materials derived from a natural source or are "nature-equivalent." In particular, there is a need for new emulsifier systems that fulfill these needs, and also allow the formation of stable emulsions with a variety of cosmetic lipids. Additional performance benefits that are needed from such a cosmetic emulsifier are good dispersibility in the water phase of an emulsion and compatibility with a low pH formulation. Further features that are desirable are (liquid) pourability at room temperature for ease of processing, no objectionable odor, and the contribution to desirable visual effects such as a pearlescent appearance.

SUMMARY OF THE INVENTION

A first embodiment of the present invention concerns a composition comprising a salt of formula 1:

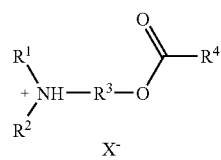

wherein $R^1$ and $R^2$ are independently a $C_1$-$C_6$ alkyl,
$R^3$ is a divalent $C_2$-$C_6$ alkyl,
$R^4$ is a $C_5$-$C_{24}$ alkyl, alkenyl, dienyl, $C_6$-$C_{24}$ trienyl, or $C_8$-$C_{24}$ tetraenyl or a mixture thereof, and
$X^-$ is adipate, pimelate, suberate, azelate, sebacate, phthalate, isophthalate, terephthalate, benzoate, 4-hydroxybenzoate, gallate, ferulate, cholate, glucuronate, alpha-lipoate, dihydrolipoate, or mixtures thereof.

Another embodiment concerns a cosmetic formulation comprising the salt described above and a cosmetically acceptable carrier.

Yet another embodiment concerns an emulsion comprising the salt described above, a water phase and an oil phase.

Another embodiment concerns a process for preparing an amino-ester salt comprising:
a) esterifying an amino-alcohol with an acid or ester of formula RCOX', wherein X' is a selected from hydroxyl or lower alcohol to obtain an ester of formula (2):

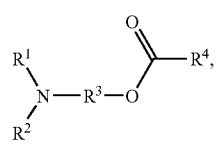

b) salifying the ester of formula (2) by contacting the reaction mixture derived from step (a) with HX" acid, wherein X" is selected from the group consisting of adipate, pimelate, suberate, azelate, sebacate, phthalate, isophthalate, terephthalate, benzoate, 4-hydroxybenzoate, gallate, ferulate, cholate, glucuronate, alpha-lipoate, dihydrolipoate, and mixtures thereof in order to obtain the salts of formula (1)

wherein $R^1$ and $R^2$ are independently a $C_1$-$C_6$ alkyl,
$R^3$ is a divalent $C_2$-$C_6$ alkyl,
$R^4$ is a $C_5$-$C_{24}$ alkyl, alkenyl, dienyl, $C_6$-$C_{24}$ trienyl, or $C_8$-$C_{24}$ tetraenyl or a mixture thereof.

DETAILED DESCRIPTION OF THE INVENTION

An embodiment of the invention concerns salts of formula 1:

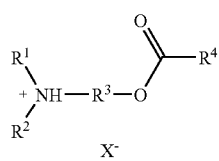

wherein $R^1$ and $R^2$ are independently $C_1$-$C_6$ linear or branched alkyl, $R^3$ is a divalent straight or branched chain $C_2$-$C_6$ alkyl, $R^4$ is a $C_5$-$C_{24}$ linear or branched alkyl, alkenyl, dienyl, $C_6$-$C_{24}$ trienyl, or $C_8$-$C_{24}$ tetraenyl or a mixture thereof, and $X^-$ is an organic carboxylate anion with six or more carbons.

A further aspect of the present invention is a solvent-free biocatalytic process for preparing the salt of formula 1 which comprises the following steps:
a) esterifying the amino-alcohol with a fatty acid or fatty acid lower alkyl ester using an enzyme catalyst, thus obtaining the ester of formula 2:

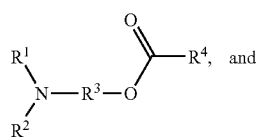

and
b) salifying the ester of formula 2 by contacting the reaction mixture derived from step (a) with HX' acid, wherein HX'=a carboxylic acid containing 6 or more carbons (excluding salicylate and mandelate) in order to obtain the salts of formula 1.

Another embodiment according to the present invention comprises an amino-ester salt represented by the general formula 1:

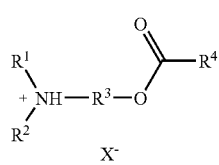

wherein $R^1$ and $R^2$ are independently selected from branched- and straight-chain $C_1$-$C_6$ alkyl, $R^3$ is selected from divalent straight or branched-chain substituted or unsubstituted $C_2$-$C_6$ alkyl, $R^4$ is selected from substituted and unsubstituted, branched- and straight-chain saturated $C_5$-$C_{24}$ alkyl, substituted and unsubstituted, branched- and straight-chain $C_5$-$C_{24}$ alkenyl, substituted and unsubstituted, branched- and straight-chain $C_5$-$C_{24}$ dienyl, substituted and unsubstituted, branched- and straight-chain $C_6$-$C_{24}$ trienyl, and substituted and unsubstituted, branched- and straight-chain $C_8$-$C_{24}$ tetraenyl or mixtures thereof, and $X^-$ is an organic carboxylic acid anion containing 6 or more carbons but is not salicylate or mandelate.

The divalent radical which may be represented by $R^3$ may be straight or branched-chain aliphatic hydrocarbon radicals containing between 2 and about 6 carbon atoms and may be substituted, for example, with one to three groups selected from $C_1$-$C_6$-alkoxy, cyano, $C_2$-$C_6$-alkoxycarbonyl, $C_2$-$C_6$-alkanoyloxy, hydroxy, hydroxyalkyl, aryl, heteroaryl, thiol, thioether, and halogen. The terms "$C_1$-$C_6$-alkoxy", "$C_2$-$C_6$-alkoxycarbonyl", and "$C_2$-$C_6$-alkanoyloxy" are used to denote radicals corresponding to the structures —$OR^5$, —$CO_2R^5$, and —$OCOR^5$, respectively, wherein $R^5$ is $C_1$-$C_6$-alkyl or substituted $C_1$-$C_6$-alkyl.

The alkyl, alkenyl, dienyl, trienyl, and tetraenyl groups which may be represented by $R^4$ may be straight- or branched-chain aliphatic hydrocarbon radicals containing up to about 24 carbon atoms and may be substituted, for example, with one to three groups selected from $C_1$-$C_6$-alkoxy, cyano, $C_2$-$C_6$-alkoxycarbonyl, $C_2$-$C_6$-alkanoyloxy, hydroxy, aryl, heteroaryl, thiol, thioether, and halogen.

The $X^-$ group is an organic acid anion containing 6 or more carbons, such as adipate, pimelate, suberate, azelate, sebacate, phthalate, isophthalate, terephthalate, benzoate, 4-hydroxybenzoate, gallate, ferulate, cholate, glucuronate, alpha lipoate or dihydrolipoate.

Examples of the compounds of the invention include those represented by formula 1 wherein acyl group $R^4$—Co is linoleoyl, stearoyl, linolenoyl, conjugated linoleoyl, palmitoyl, palmitoleoly and oleoyl or mixtures thereof.

Another embodiment of the present invention involves the solvent-free biocatalytic synthesis of fatty acid esters of amino-alcohols. The compounds of the invention can be prepared by the process of the invention by carrying out a solvent-free esterification, at mild temperatures in the presence of an enzyme catalyst. The salification step is then performed by contacting an organic carboxylic acid with the amino-alcohol fatty acid ester, resulting in neutralization of the amine portion of the amino-alcohol fatty acid ester to form the salt. Benefits of the enzymatic process include mild processing conditions. No undesirable byproducts that may contribute to color or odor are formed in the process. No organic solvents are used in the process, and so no organic solvents are present in the final product—a feature especially important to a cosmetic ingredient. The use of toxic or hazardous reagents is avoided.

A process according to the present invention comprises the reaction of the amino-alcohol with a long chain fatty acid or fatty acid ester to afford amino-ester 2.

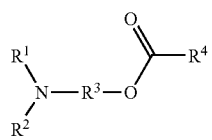

2

The process is carried out without solvent. The process may be carried out at a temperature between about −100° C. and the boiling point of the amino-alcohol, between about 0-60° C., or between about 20-50° C. The amount of amino-alcohol may be between 0.85 and 20 equivalents based on long-chain acid or long-chain ester, between 0.85 and 10 equivalents, or between 0.85 and 2 equivalents. The enzyme used in the process is chosen from a protease, a lipase, or an esterase. The lipases may be in the form of whole cells, isolated native enzymes, or immobilized on supports. Examples of these lipases include but are not limited to Lipase PS (from *Pseudomonas* sp), Lipase PS-C (from *Psuedomonas* sp immobilized on ceramic), Lipase PS-D (from *Pseudomonas* sp immobilized on diatomaceous earth), Lipoprime 50T, Lipozyme TL 1M, or Novozyme 435 (from *Candida antarctica* immobilized on acrylic resin). Removal of the water or alcohol byproducts can be done chemically via a water or alcohol absorbent (e.g., molecular sieves) or by physical removal of the water or alcohol. This by-product removal can be done by evaporation, either by purging the reaction mixture with an inert gas such as nitrogen, argon, or helium, or by performing the reaction at reduced pressures, or both, as these conditions can afford >98% conversion of amino alcohol to amino ester. The preferred pressure for the reaction is between 1 torr and ambient pressure, more preferable between 50 torr and ambient pressure.

The use of short chain alcohol esters of fatty acids is beneficial to the success of the enzymatic esterification of the amino alcohol. Unmodified fatty acids may be used in the enzymatic esterification, however the acid forms a salt with the amino alcohol and limits the efficiency of the reaction. Short chain esters of the fatty acid reagent can be produced by any practical method, including the solvolysis of triglycerides in the presence of a lower alcohol and a base or enzyme catalyst as is known in the art. Examples of lower alcohols are $C_1$-$C_4$ alcohols such as methanol, ethanol, 1-propanol, 2-propanol, 1-butanol, 2-butanol, and Isobutanol.

The amino-ester product of the process may be isolated using methods known to those of skill in the art, e.g., extraction, filtration, or crystallization.

The final salt 1 is formed by contacting the amino ester with an organic carboxylic acid containing 6 or more carbons. The carboxylic acid is used at 0.3 to 10 molar equivalents with respect to the amino ester, between 0.5 and 2.0 molar equivalents, or between 0.8 and 1.0 molar equivalents with respect to the amino ester. This contacting is done in the absence of solvent and is performed between 0 and 100° C. The time for contacting is between 1 and 24 h, with higher temperature resulting in shorter reaction times.

Another embodiment of the invention is the use of the amino-ester salts as emulsifiers. Fatty acid esters of amino-alcohols are molecules possessing both hydrophilic and hydrophobic regions, making them useful as emulsifiers in formulations containing an oil phase and water phase, such as cosmetic formulations for the skin such as creams, lotions, moisturizers and body washes. Cosmetic lipids include triglycerides (oils), fatty alcohols and fatty acids and esters between such, and natural waxes such as beeswax. Such formulations can contain between about 0.001 weight % and about 20 weight %, between about 0.01 weight % and about 15 weight %, or even between about 0.1 weight % and 10 weight % of the amino-ester salts.

As an example, the present inventors have discovered that certain salts of DMAE fatty acid esters are odor-free derivatives that are especially useful as emulsifiers for formulating skin care emulsions. Beeswax, soy wax and cetyl alcohol were generally compatible oil phases for this group of emulsifiers. In addition, the pH of a water dispersion of the salt is significantly different than that of the free amino-ester. A 5 wt % dispersion of DMAE rice bran oil fatty acid esters in water has a pH of 9. Carboxylic acid salts of DMAE rice bran oil fatty acid esters are also easily dispersed or dissolved in water, and the pH of a 5 wt % dispersion/solution is between 2 and 6. The pH of a formulation can have a profound effect on the bioavailability of components in the formula and on skin irritation, with acidic components such as glycolic acid, lactic acid, ascorbic acid and salicylic acid being more effective in lower pH formulations. The normal pH of human skin is around 4, suggesting that formulations with a pH near this value will be more compatible with the skin. Finally, several of the DMAE fatty acid ester salt emulsifiers formed an emulsion in the presence of cetyl alcohol that has a desirable pearlescent appearance.

Whereas the DMAE fatty acid esters still exhibit a strong "fishy" amine odor, the salts, whether liquid or solid at room temperature, have very low to no detectable amine odor.

EXAMPLES

The following examples further illustrate the present invention. All percentages given are by weight unless otherwise specified.

Example 1

Fatty Acid Esters of 2-dimethylaminoethanol (DMAE) EX000194-165

DMAE mixed fatty acid esters were made biocatalytically from DMAE (CAS 108-01-0) and rice bran oil fatty acid ethyl esters. Fatty acid ethyl esters of rice bran oil (222 grams) were combined with 1.5 molar equivalents of DMAE (96 grams) in a reaction vessel. An immobilized enzyme catalyst, Novozym 435 (6.3 grams), was added to the reaction mixture. The reaction mixture was heated to 50 degrees C. with stirring. The reaction was additionally purged with a constant stream of nitrogen to agitate the mixture and strip off the ethanol by-product to drive the reaction to completion. The progress of the enzymatic reaction, as assessed by the presence of residual fatty acid ethyl esters, was monitored by gas chromatography. The reaction was stopped when the concentration of residual fatty acid ethyl esters was less than 5%. The immobilized enzyme catalyst was removed from the reaction mix by filtration, and the product was used without requiring further purification.

$^1$H NMR (CDCl$_3$) d 5.4-5.25 (m, 2-3H); 4.175 (t, 2H, J=5.95 Hz); 2.770 (t, <1H, J=5.95 Hz); 2.573 (t, 2H, J=5.95 Hz); 2.324 (t, 2H, J=7.33 Hz); 2.289 (s, 6H); 2.1-1.95 (m, 4H); 1.65-1.55 (m, 2H); 1.2-1.05 (m, ca. 24H); 0.95-0.8 (m, 3H).

The fatty acids were derived from rice bran oil, and this naturally-derived product will vary slightly in composition. The approximate composition of DMAE "oryzanate" is:

43% DMAE oleate (CAS 40817-22-9)

33% DMAE linoleate (CAS 116865-17-9)

21% DMAE palmitate (CAS 40817-19-4

2% DMAE stearate (CAS 39840-30-7)

Example 2

Salts from the DMAE Fatty Acid Esters (EX000111-063)

A variety of carboxylic acids readily formed a salt with DMAE oryzanate fatty acid esters. Salts were formed by combining equimolar ratios of the carboxylic acid and DMAE oryzanate fatty acid esters (assuming an average molecular weight of 353.58 for the mixture of DMAE rice bran oil fatty acid esters). The salts formed spontaneously after mixing the DMAE fatty acid ester and carboxylic acid in equimolar ratios at room temperature, or after heating briefly at temperatures up to 50 degrees C., and were either waxy solids or liquids at room temperature.

Whereas the DMAE rice bran oil fatty acid esters still exhibit a strong "fishy" amine odor, the salts, whether liquid or solid at room temperature, have very low to no detectable amine odor. In addition, the pH of a water dispersion of the compound has changed. A 5 wt % dispersion of DMAE rice bran oil fatty acid esters in water has a pH of 9. Carboxylic acid salts of DMAE rice bran oil fatty acid esters are also easily dispersed or dissolved in water, and the pH of a 5 wt % dispersion/solution is between 2 and 6. The normal pH of human skin is around 4, suggesting that formulations with a pH near this value will be more compatible with the skin.

|  | MW of acid | Form of salt with "DMAE rice branate" fatty acid esters | pH in water (5 wt %) |
| --- | --- | --- | --- |
| Adipic acid | 146.14 | Liquid | 4 |
| Alpha lipoic acid | 206.33 | Liquid | 5 |
| Azelaic acid | 188.22 | Liquid | 4 |
| Benzoic acid | 122.12 | Liquid | 4 |
| Cholic acid | 408.57 | Waxy solid | 6 |
| Citric acid | 192.12 | Waxy solid | 3 |
| Ferulic acid | 194.18 | Liquid | 5 |
| Fumaric acid | 116.07 | Waxy solid | 3 |
| Gallic acid | 170.02 | Waxy solid | 4 |
| D-Glucuronic acid | 194.14 | Waxy solid | 3 |
| Glycolic acid | 76.05 | Liquid | 4 |
| 4-Hydroxybenzoic acid | 138.12 | Liquid | 4.5 |
| Malic acid | 134.08 | Waxy solid | 3.5 |
| Malonic acid | 104.06 | Waxy solid | 3 |
| Oxalic acid | 90.03 | Waxy solid | 2 |
| Salicylic acid | 138.12 | Liquid | 3.5 |
| Succinic acid | 118.09 | Liquid | 4 |
| L-Tartaric acid | 150.09 | Waxy solid | 4 |

Example 3

Emulsions Made from the DMAE Fatty Acid Ester Salts (EX000111-063)

Simple emulsions were made from the salts of the DMAE fatty acid esters. Water phase: The DMAE fatty acid ester salts were dispersed in water at a final concentration of 5 wt %. The DMAE ester salts that are liquid at room temperature readily disperse in water, while agitation facilitates dispersion of the waxy solids.

The following lipids were used as the oil phase:

Beeswax; Cetyl alcohol; Soy wax (partially hydrogenated soybean oil); and Cetearyl rice branate (cetyl and stearyl esters of rice bran oil fatty acids). The oil phase was added to the water phase to afford 10 wt % oil phase and heated, as necessary, to melt the lipid.

An emulsion was prepared by homogenizing the combined oil and water phases for 30 seconds with a hand-held homogenizer (IKA Model UltraTurrax T-8). The stability and appearance of the resulting emulsion was assessed visually after 24 hours at room temperature. The results are summarized in the Table below. Stable emulsions were formed by the addition of the salts of the DMAE fatty acid esters tested. Beeswax, soy wax and cetyl alcohol were generally compatible oil phases for this group of emulsifiers. The DMAE rice bran fatty acid esters salt made with alpha-lipoic acid was additionally useful for emulsifying palm oil, while the benzoate salt was useful for making a stable emulsion with the emollient ester mixture cetearyl rice branate.

In addition, several of the DMAE fatty acid ester salt emulsifiers formed an emulsion in the presence of cetyl alcohol that has a desirable pearlescent appearance. These included the biazelate, benzoate and 4-hydroxybenzoate salts.

| | Stability of emulsion, 24 h, room temp. 10 wt % oil phase in water containing 5 wt % emulsifier (S = stable; P = pearlescent appearance) | | | | |
|---|---|---|---|---|---|
| Salt of DMAE rice bran fatty acid esters | (A) Palm oil | (B) Bees wax | (C) Cetyl alcohol | (D) Soy wax | (E) Cetearyl rice branate |
| Citrate | | S | S | S | |
| Tartrate | | S | S | S | |
| Bitartrate | | S | S | S | |
| (bi)Azelate | | | S, P | S | |
| (bi)Adipate | | S | S | | |
| (bi)Malate | | S | S | S | |
| (bi)Malonate | | S | S | | |
| (bi)Oxalate | | S | S | S | |
| (bi)Fumarate | | S | S | S | |
| Benzoate | | S | S, P | S | S |
| Gallate | | S | S | S | |
| Ferulate | | | | S | |
| 4-hydroxy-benzoate | | S | S, P | | |
| Lipoate | S | | S | S | |
| Glucuronate | | S | S | | |

The invention has been described in detail with particular reference to preferred embodiments thereof, but it will be understood that variations and modifications can be effected within the spirit and scope of the invention.

We claim:

1. A composition comprising a salt of formula 1:

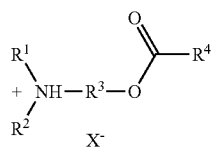

wherein $R^1$ and $R^2$ are independently a $C_1$-$C_6$ alkyl,
$R^3$ is a divalent $C_2$-$C_6$ alkyl,
$R^4$ is a $C_5$-$C_{24}$ alkyl, alkenyl, dienyl, $C_6$-$C_{24}$ trienyl, or $C_8$-$C_{24}$ tetraenyl or a mixture thereof, and
$X^-$ is adipate, pimelate, suberate, azelate, sebacate, phthalate, isophthalate, terephthalate, benzoate, 4-hydroxybenzoate, gallate, ferulate, cholate, glucuronate, alpha-lipoate, dihydrolipoate, or mixtures thereof.

2. A cosmetic formulation comprising the salt according to claim 1 and a cosmetically acceptable carrier.

3. The formulation according to claim 2, wherein the salt is present in an amount of from about 0.001 weight % to about 20 weight %.

4. The formulation according to claim 3, wherein the salt is present in an amount of from about 0.01 weight % to about 15 weight %.

5. The formulation according to claim 4, wherein the salt is present in an amount of from about 0.1 weight % to about 10 weight %.

6. The formulation according to claim 2, wherein the formulation is a cream, lotion, moisturizer or body wash.

7. An emulsion comprising the salt according to claim 1, a water phase and an oil phase.

8. The emulsion according to claim 7, wherein the salt is present in an amount from about 0.001 weight % to about 20 weight %.

9. The emulsion according to claim 8, wherein the salt is present in an amount from about 0.01 weight % to about 15 weight %.

10. The emulsion according to claim 9, wherein the salt is present in an amount from about 0.1 weight % to about 10 weight %.

11. A process for preparing an amino-ester salt comprising:
a) esterifying an amino-alcohol with an acid or ester of formula RCOX', wherein X' is a selected from hydroxyl or lower alcohol to obtain an ester of formula (2):

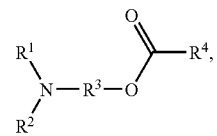

b) salifying the ester of formula (2) by contacting the reaction mixture derived from step (a) with HX" acid, wherein X" is selected from the group consisting of adipate, pimelate, suberate, azelate, sebacate, phthalate, isophthalate, terephthalate, benzoate, 4-hydroxybenzoate, gallate, ferulate, cholate, glucuronate, alpha-lipoate, dihydrolipoate, and mixtures thereof in order to obtain the salts of formula (1)

wherein $R^1$ and $R^2$ are independently a $C_1$-$C_6$ alkyl,
$R^3$ is a divalent $C_2$-$C_6$ alkyl,
$R^4$ is a $C_5$-$C_{24}$ alkyl, alkenyl, dienyl, $C_6$-$C_{24}$ trienyl, or $C_8$-$C_{24}$ tetraenyl or a mixture thereof.

12. The process according to claim 11, wherein (a) and (b) are carried out in the absence of added solvent.

13. The process according to claim 11, wherein (a) further comprises an enzyme catalyst.

14. The process according to claim 11, wherein the process is carried out at a temperature between about −100° C. and the boiling point of the amino-alcohol.

15. The process according to claim 14, wherein the temperature is between about 0° C. and about 60° C.

16. The process according to claim 15, wherein the temperature is between about 20° C. and about 50° C.

17. The process according to claim 11, wherein the amino-alcohol is present in an amount of between 0.85 and about 20 equivalents based on the acid or ester.

* * * * *